(12) United States Patent
Lyapko

(10) Patent No.: US 8,025,673 B1
(45) Date of Patent: Sep. 27, 2011

(54) NEEDLE FOR USE IN REFLEXOTHERAPY, AND AN APPLICATOR USING THE SAME

(76) Inventor: Nikolai Grigorievich Lyapko, Donetskoy (UA)

( * ) Notice: Subject to any disclaimer, the term of this patent is extended or adjusted under 35 U.S.C. 154(b) by 601 days.

(21) Appl. No.: 10/031,162

(22) PCT Filed: Jul. 13, 2000

(86) PCT No.: PCT/UA00/00023
§ 371 (c)(1),
(2), (4) Date: May 20, 2002

(87) PCT Pub. No.: WO01/05351
PCT Pub. Date: Jan. 25, 2001

(30) Foreign Application Priority Data

Jul. 15, 1999 (UA) .................................... 99074080

(51) Int. Cl.
*A61B 17/34* (2006.01)

(52) U.S. Cl. ...................................................... 606/189

(58) Field of Classification Search .................. 606/189, 606/185, 186
See application file for complete search history.

(56) References Cited

U.S. PATENT DOCUMENTS

| 2,441,682 A | * | 5/1948 | Wybrants | 601/81 |
| 4,823,806 A | * | 4/1989 | Bajada | 600/557 |
| 5,458,561 A | * | 10/1995 | Schweisfurth | 601/119 |
| 5,676,684 A | * | 10/1997 | Choi | 606/189 |

FOREIGN PATENT DOCUMENTS

SU 1264942 A * 10/1986
SU 1797889 A1 * 2/1993

* cited by examiner

*Primary Examiner* — Ryan J Severson
(74) *Attorney, Agent, or Firm* — Weiner & Burt, P.C.; Irving M. Weiner; Pamela S. Burt

(57) ABSTRACT

"A reflexotherapy applicator having needles fixed in a flat elastic base. Each needle has a core, a sharpened portion, and a thickened portion. The thickened portions are fixed in the base so that the sharpened portions protrude from the base. One or more needle groups have a partially coated core. One or more needle groups have multilayer coatings of the core and sharpened portion. One or more needle groups differ from the other groups by their materials or by the coating materials, which have different electrochemical potentials. The needles and their coatings are made from steel, copper, chromium, nickel, silver, cobalt, aluminum, magnesium, zinc, tin, titanium, vanadium, beryllium, gold, platinum, strontium, tellurium or their alloys and oxides. The needles are placed on the base so that adjacent needles are made from materials with different electrochemical potentials and are designed to contact an user's skin."

3 Claims, 4 Drawing Sheets

NEEDLE FOR USE IN REFLEXOTHERAPY, AND AN APPLICATOR USING THE SAME

FIELD OF INVENTION

Figure 1:
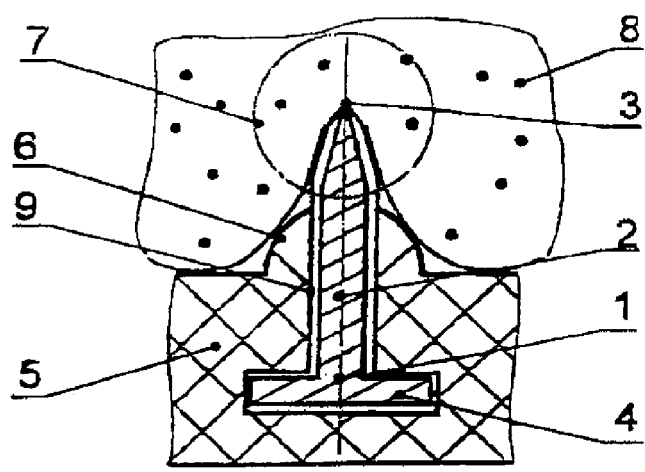

The present invention relates to devices intended for stimulating specific reflex areas or individual reflex points of the human body, and particularly to needles for use in reflexotherapy (i.e. acupuncture and application acupressure) and in applicators, and may be used both at medical institutions and under home conditions. The needles may be used either as component parts of applicators or as independent instruments for practising acupuncture.

BACKGROUND OF THE INVENTION

The most relevant device to the proposed needle comprises a needle having a base in the form of a rod member provided with a sharpened portion at one end and a head portion at the opposite end thereof, said rod being made of steel, copper, chromium, nickel, or silver, and with one layer of solid coat made of chromium, copper, silver, or nickel over the whole base of the needle (SU-A-1797889).

Solid coat of the needle base restricts the possibilities of electrophoresis since only one microelement is delivered to the user's body (either from the needle surface or from the base thereof if the needle is not provided with a coat), as well as insignificant amount of the needle base microelement due to diffusion through through the coat. Besides, no microcurrents are available within any needle, thereby eliminating its electrical effect on a corresponding area of the user's body and causing insufficient intensity of electrophoresis. In addition, the presence of a solid coat results in a rather high consumption of valuable coating materials, e.g. silver. The narrow range of materials (i.e. copper, nickel, silver) considerably restricts selection of microelements required by the user.

Known in the art is an applicator comprising a base member and needles fixed therein and provided with sharpened portions and heads, wherein needle bases are made of steel, copper, chromium, nickel, or silver, and coats are made of copper, chromium, nickel, or silver; these materials, upon being brought into contact with epidermis, form galvanic couples (SU-A-1797889).

This applicator provides a limited set of materials, thereby restricting the set of microelements to be delivered to the user's body, i.e. possibilities of electrophoresis; in addition, it restricts the possibility of presetting required parameters of microcurrents. Application of coats to the whole bases of needles provides the possibility of generating microcurrents only between needles made of dissimilar materials, while eliminating such microcurrents developed between dissimilar materials of individual needles in the user's body, thereby eliminating generation of a three-dimensional complicated heterogeneous electrical field in the user's epidermis; this in turn restricts the efficiency of application and results in insufficient smoothing of the electrical field, disturbed by a disease, in the user's skin upon application, and causes insufficient efficiency of electrophoresis.

BRIEF DESCRIPTION OF THE INVENTION

The main object of the present invention consists in improving the needle for use in reflexotherapy by way of developing an area of contact thereof with the user's body, said area consisting of at least two materials having different electrochemical potentials to provide the flow of microcurrents between these materials, and by expanding the set of materials used to produce the needle base and coats, thereby ensuring both mechanical and electrical action of the needle on a corresponding area of the user's body; providing a reasonable selection of materials for the needle base and coats, required to preset microcurrent parameters; expanding the possibilities of electrophoresis through the transfer of a broader set of microelements to the user's body, and improving electrophoresis intensity due to microcurrents.

Another object of the present invention consists in improving the applicator by way of providing at least some of the needles with solid and/or partial coats, while forming in the case of a partial coat and close to the sharpened portion an area consisting of at least two materials having different electrochemical potentials, i.e. an area of contact between the needles and the user's epidermis, and expanding the set of materials used for making needle bases and coats, thereby generating a three-dimensional complicated heterogeneous electrical field of microcurrents between the needles, providing microcurrents between the bases of individual needles and coats, thereof; presetting required parameters of microcurrents, smoothing by way of electrophoresis the uniformity of electrical field of the user's skin, said uniformity being disturbed by a disease; delivering a greater set of microelements to the user's body, and intensifying the process of this delivery.

The object set forth is achieved by that in the needle for use in reflexotherapy, having a base in the form of a rod member provided with a sharpened portion at one end thereof, said rod being made of steel, copper, chromium, nickel, or silver, and with coat made of chromium, nickel, copper, or silver, according to the invention the coat of the needle base is made partial with formation, close to the sharpened area, of a region composed by at least two materials having different electrochemical potentials, while the base and the coat are made of chemical elements selected from a group additionally including cobalt, aluminium, magnesium, zinc, tin, titanium, vanadium, beryllium, gold, platinum, palladium, strontium, tellurium, and alloys and oxides thereof.

Partial coat of the needle base with the formation of an area close to the needle sharpened portion, i.e. an area of contact between the needles and the user's body, consisting of two or more materials having different electrochemical potentials results in generation, in the user's body, of galvanic currents between these materials (needle base and coat perform the function of electrodes, and the fluid contained in the user's body and particularly in epidermis, the function of electrolyte), said currents flowing in the planes perpendicular to the user's skin, thereby ensuring both mechanical and electrical action of a needle on a corresponding area of the user's body, as well as expanding the possibilities of electrophoresis (microelements are transferred to the user's body both from the needle base and from coat/coats) and improving intensity thereof. Expansion of the set of chemical elements expands the possibilities of electrophoresis since it becomes possible to select elements necessary for each individual user from the wider set of such elements. In addition, it permits the use of inexpensive, hard and durable materials such as steel, copper, brass etc. for the needle base, and soft, expensive and rare materials such as tin, gold, silver etc. for coats, the use of expensive and rare materials being possible in substantially smaller amounts; besides, it provides the possibility of generating microcurrents with preset parameters through an appropriate combination of materials for needle bases and coats.

Here, the area of the needle surface from the sharpened portion side can be formed either by the needle base and coat or by coat which may be applied either to the needle base except the sharpened portion thereof, or only to the sharpened portion.

Such arrangement provides the simplest way of obtaining a potential difference between the needle base and coat. In addition, application of coats from valuable and rare materials (gold, silver, platinum, palladium etc.) only to the sharpened portion of the needle provides substantial savings of these materials.

The area of the needle surface from the sharpened portion side is the most expedient to be formed by the needle base and several layers of coats of various materials, each layer being stripped at the end face thereof close to the needle sharpened portion.

Figure 9:
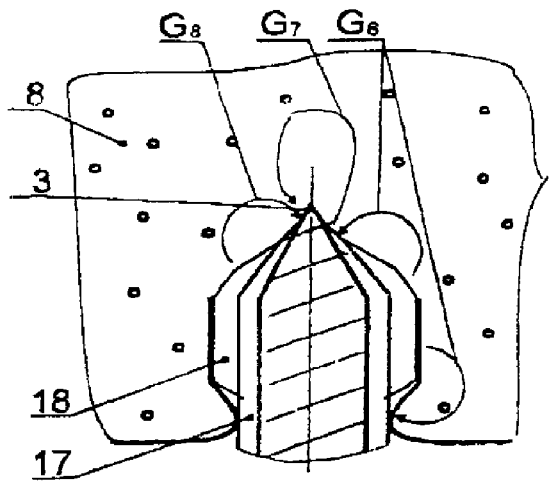
Figure 10:
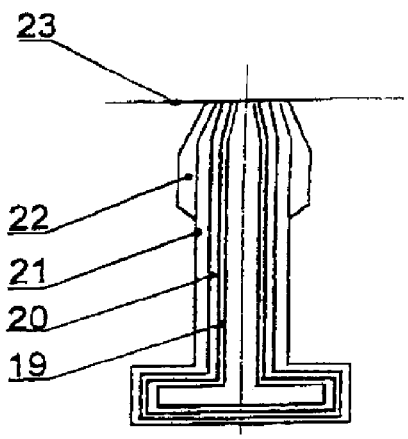
Figure 11:
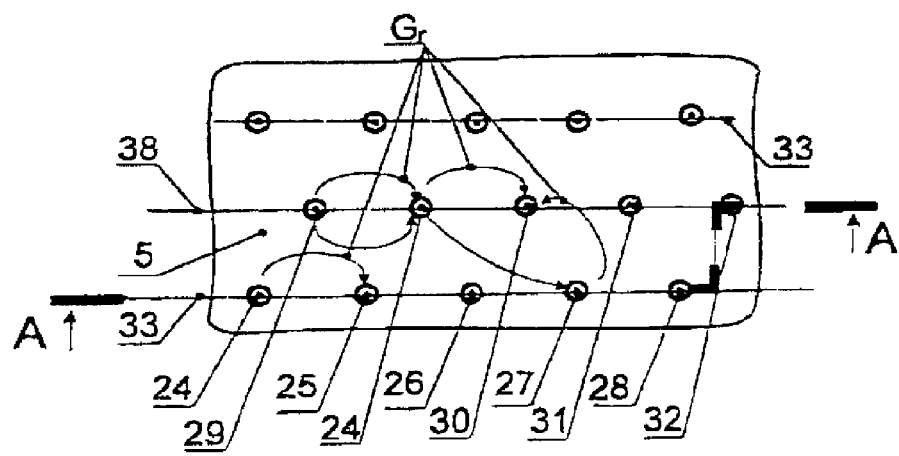
Figure 12:
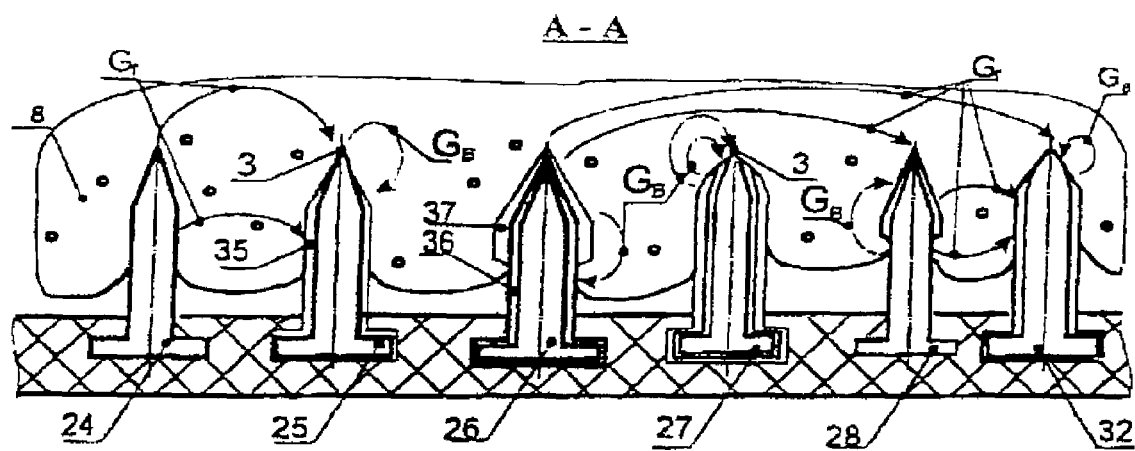

The potential difference between each pair of adjacent coat layers and pairs of other layers gives rise to a combination of various galvanic microcurrents in the point of contact between the needle and epidermis, i.e. to heterogeneous electrical field; this phenomenon results in an increase of electrical action of the needle on epidermis and provides transfer of microelements of all the coat layers into the body, said transfer being intensified by galvanic microcurrents. Such arrangement provides maximum increase of the effects of reflexotherapy and electrophoresis.

It would be also expedient to construct the area of the needle surface from the sharpened portion side from a multilayer coat applied to the whole needle base, and a coat applied on the top of the above multilayer coat in the sharpened portion area.

Such arrangement will cause generation of a galvanic microcurrent between the coats applied to the needle sharpened portion and the base thereof, and resulting intensification of transfer of microelements from both external layers of coats and from internal layers due to diffusion. In addition, it permits the use of materials that are useful for reflexotherapy but have insufficient hardness and durability, in the form of coats applied to a hard and durable base.

Here, in a portion of the needle surface, composed from at least one layer of coat applied to the whole needle base, and a coat applied to the needle sharpened portion on top of the above one layer, each layer of coat can be stripped at the end face thereof close to the needle sharpened portion, thereby increasing the number of microcurrents and intensifying electrophoresis.

In addition, one or more coat layers can be applied by spraying, thereby producing dense or loose layers.

Looseness of coat layers, and particularly external layer, promotes outward diffusion of microelements from internal layers.

The object set forth is also achieved by that in applicator having a base member and needles fixed therein, each needle having a base in the form of a rod member provided with a sharpened portion and a head portion, said needle bases being made of steel, copper, chromium, nickel, or silver, and with a coat made of chromium, nickel, copper, or silver, according to the invention at least some needles are provided with solid and/or partial coats, while forming in the case of a partial coat and close to the sharpened portion an area consisting of at least two materials having different electrochemical potentials, and needle bases and coats are made of chemical elements selected from a group additionally including cobalt, aluminium, magnesium, zinc, tin, titanium, vanadium, beryllium, gold, platinum, strontium, tellurium, and alloys and oxides thereof. Microcurrents between needle bases and coats are flowing in the planes that pass along the longitudinal axes of needles, and microcurrents between the needles, in the planes that are perpendicular or inclined to the above planes, thereby generating a three-dimensional complicated heterogeneous electrical field in the epidermis.

An increase of the set of chemical elements results in expansion of possibilities of electrophoresis since it permits to select required elements from a wider range thereof, and to use the whole set of such elements in a single applicator, particularly in case of partial multilayer coating of individual needle bases with different materials, where a number of needle bases and coats are brought into contact with the user's epidermis; the use of a wide set of materials permits to preset required-parameters of the electrical field through an appropriate combination of materials of needle bases and coats. In addition, the above microcurrents accelerate the transfer of microelements to the user's body, thereby increasing electrophoresis intensity. Diversity of electrobiochemical conditions of epidermis during interaction thereof with various materials of needle bases causes an independent adjustment of microcurrent parameters between the needles made of different materials, and microcurrents between different materials of individual needles, as well as electrophoresis parameters. A higher heterogeneity of the electrical field causes smoothing of the electrical field in the user's skin, disturbed by a disease.

It is expedient to arrange needles in the applicator in such way that adjacent needles comprise different base and coat materials.

Such arrangement of needles in the applicator results in generation, in various points of contact between the body and individual needles, of microcurrents having different parameters, and the contact between the body and various materials of individual needles, thereby increasing heterogeneity of the electrical field and expanding the range of microelements transferred from needle bases and coat layers to the user's body; in addition, it accelerates electrophoresis and intensifies smoothing, as a result of reflexotherapy, of the violated uniformity of the electrical field of the user's skin.

BRIEF DESCRIPTION OF DRAWINGS

The invention is further described in more detail in terms of specific embodiments thereof and with reference to the accompanying drawings, in which:

FIG. 1 shows a cross-section of the schematic drawing of a needle provided with a single-layer coating applied to the needle base except the sharpened portion thereof, or only to the sharpened portion, together with fragments of applicator and user's body;

FIGS. 2 and 3 demonstrate schematic drawings of stripped sharpened portion of the needle of the invention, shown in FIG. 1;

FIG. 4 shows schematic drawing of generation of galvanic microcurrent in the epidermis between the base and coat of the needle of the invention, shown in FIG. 1;

FIG. 5 demonstrates schematic drawing of the needle of the invention provided with coat only on the sharpened portion thereof;

FIG. 6 shows schematic drawing of the needle of the invention, provided with coated sharpened portion and stripped apex of this portion;

FIG. 7 demonstrates schematic drawing of the needle of the invention, provided with a two-layer coat applied to the needle base except the sharpened portion thereof;

FIG. 8 shows schematic drawing of the needle of the invention, provided with a single-layer coat of the needle base and the coat applied to the sharpened portion on top of the first layer;

FIG. 9 demonstrates schematic drawing of the needle of the invention, provided with a single-layer coat of the needle base, the coat applied to the sharpened portion on top of the first layer, and the apex of the sharpened portion that contains no coat;

FIG. 10 shows schematic drawing of the needle of the invention, provided with a three-layer coat of the needle base, the coat applied to the sharpened portion on top of the above three layers, and the apex of the sharpened portion that contains no coat;

FIG. 11 demonstrates top view of a fragment of the schematic drawing of the applicator of the invention;

FIG. 12 shows section A-A of the applicator of the invention, shown in FIG. 11.

PREFERRED EMBODIMENT OF THE INVENTION

Needle 1 of the applicator (FIG. 1) comprises rod member 2 provided with sharpened portion 3 at one end and head 4 at the other end thereof. Needle 1 is fixed in base member 5 of the applicator so that its part provided with sharpened portion 3 protrudes above surface 6 of base member 5. Area 7 close to sharpened portion 3, i.e. the area of contact between needle 1 and epidermis 8, includes either side surface of needle 1 from sharpened portion 3 to surface 6 or a portion of this surface, depending on required depth of penetration of needle 1 into epidermis 8. The depth of penetration depends on a pressure acting on the applicator, density of needles arrangement and sharpness of their sharpened portions, area 7 including at least two materials having different electrochemical potentials; in the given case, as shown in FIG. 1, these are material of needle 1 base and material of layer 9 of the coat applied to the base of needle 1 except sharpened portion 3 thereof. In embodiments of the invention, such coat may be applied to the base of a needle except e.g. a part of the sharpened portion or except sharpened portion 3 and a part of rod 2 close to sharpened portion 3 since it is rather difficult to coat the whole rod with exact exception of sharpened portion 3. The base of needle 1 can be made of iron or alloy thereof; e.g. steel, and layer 9 may be made e.g. of nickel, chromium, zinc, or copper. Needle 1 may be made of copper or alloy thereof, e.g. of brass, and layer 9 of the coat may be made of nickel, chromium, or silver. Here, it is expedient to coat nickel with chromium. The coat may be applied with the use of any method known in the art, e.g. by dipping, spraying, or galvanising.

Figure 2:
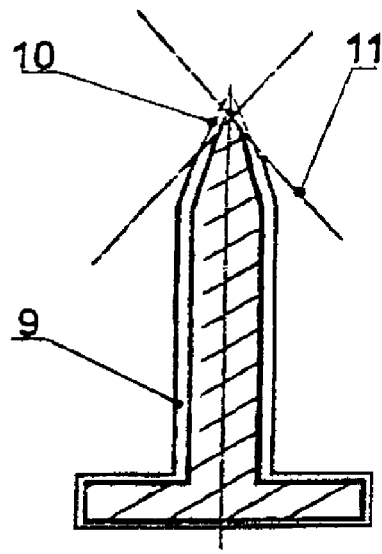
Figure 3:
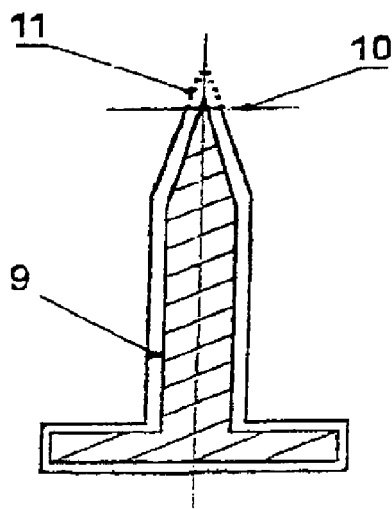

It is expedient to apply layer 9 of the coat to whole needle 1, including sharpened portion 3 thereof, and then to strip sharpened portion 3 by removing the coat e.g. by grinding off the coat 9 next to sharpened portion 3 to form a cone (FIG. 2), said grinding off being carried out over conical surface 10 with removal of part 11 of layer 9, or by cutting off the coat over plane 10 (FIG. 3) with removal of part 11 of layer 9.

Operation of the needle of the invention consists in the following.

Figure 4:
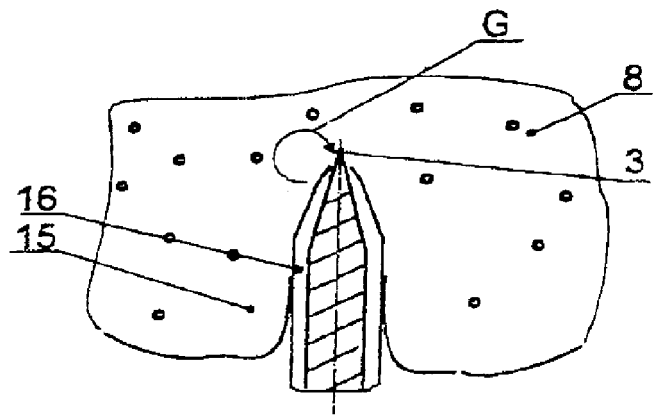

Upon penetration of needle 1 (FIG. 4) into the user's body, particularly into epidermis 8 comprising a liquid ionised constituent, the difference of electrochemical potentials between the material of the base of needle 1 and the material of layer 9 of the coat results in generation of galvanic microcurrent G, i.e. the proposed design of the needle develops conditions where a galvanic cell with electrodes (material of the base of needle 1 and layer 9 of the coat) interacts with electrolyte (liquid ionised part of body 8). In other words, mechanical action caused by penetration of needle 1 into epidermis 8 is additionally accompanied by the action of galvanic microcurrent, G, of the electrical field on the user's body. In addition, the possibility is provided to carry out transfer of microelements both from sharpened portion 3 of the needle and from layer 9 of the coat, such transfer being considerably intensified through the presence of galvanic microcurrent, G. Thus, intensification of the effects of both reflexotherapy and electrophoresis are achieved.

Figure 5:
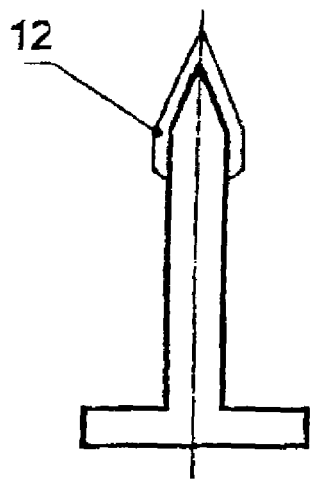

In another preferred embodiment of the present invention, shown in FIG. 5, coat 12 may be applied to sharpened portion 3 of needle 1. The base of needle 1 and coat 12 may be made of the same materials as specified in the previous embodiment of the invention. This embodiment however is expedient to be carried out when introducing precious and rare materials such as platinum, gold, silver, and platinum in the user's body, since such arrangement results in considerable decrease of their consumption (only sharpened portion 3 rather than the whole base of needle 1 are coated with these metals).

The needle made in compliance with this embodiment operates similarly to the previous case.

Figure 6:
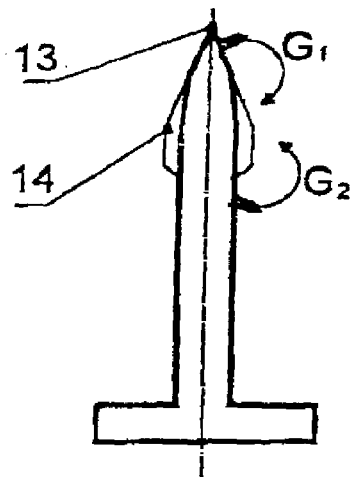

When stripping a part of sharpened portion 3 as shown in FIG. 6, the following galvanic couples are formed: between apex 13 of sharpened portion 3 of needle 1 and coat 14 (galvanic microcurrent $G_1$), and between coat 12 and rod 2 (galvanic microcurrent $G_2$), thereby intensifying the electrical action of needle 1 and electrophoresis.

Figure 7:
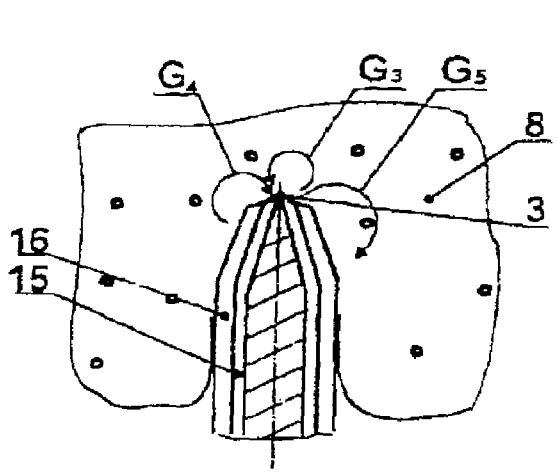

The area of contact between needle 1 and user's epidermis 8 (FIG. 7) may include the base of needle 1 and several, e.g. two layers 15 and 16 of coat, applied to said base and stripped close to sharpened portion 3 of needle 1. In this case, three different galvanic couples are formed: layer 15 of coat—sharpened portion 3 (galvanic microcurrent $G_3$); layer 16—sharpened portion 3 (galvanic microcurrent $G_4$), and layer 15—layer 16 (galvanic microcurrent $G_5$). This fact further intensifies electrical action of the needle and provides transfer of microelements from all three materials to epidermis 8, i.e. needle 1 and layers 15 and 16. It should be also noted that transfer of microelements from rod 2 and layer 15, through layer 16 and into the user's body is also carried out due to diffusion, the amount of this transfer being substantial as a result of large contact area between rod 2 and layer 15, between layers 15 and 16, and between layer 16 and user's body. Needle 1 may be provided with still more layers of coat, which fact results in intensification of the action caused by electrical fields and electrophoresis, since in this case more various microelements are transferred to the user's body.

Figure 8:
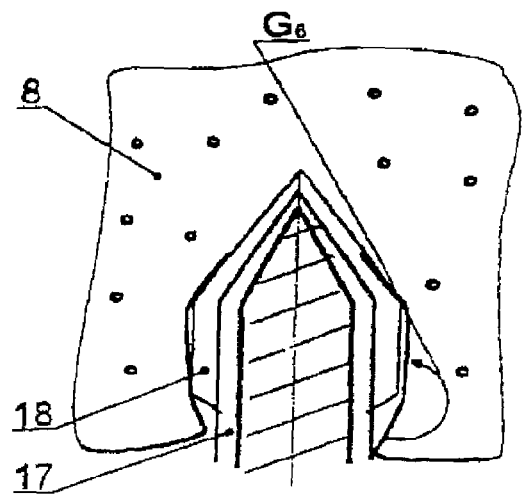

As shown in FIG. 8, the area of contact between needle 1 and body 8 may include one coat layer 17 applied to the whole base of needle 1, and coat layer 18 on sharpened portion 3 of needle 1, applied on the top of layer 17. In this case, layer 17—layer 18 galvanic couple is formed (galvanic microcurrent $G_6$), and transfer of microelements from the base of needle 1 and layers 17, 18 occurs by diffusion, due to a larger area of contact between all the surfaces, i.e. in this embodiment electrophoresis outweighs the galvanic effect.

The latter of the above-disclosed embodiments of the invention may be somewhat modified if sharpened portion 3 is left without layers 17, 18, e.g. by way of grinding them off (FIG. 9) (or due to quick wear during the use of applicator). In this case, $G_6$ microcurrent between layers 17, 18 is supplemented by $G_7$ galvanic microcurrent between layer 17 and sharpened portion 3, and $G_8$ galvanic microcurrent between layer 18 and sharpened portion 3. This intensifies the electrical action of needle 1 on epidermis 8 and results in a more pronounced electrophoretic effect.

As shown in FIG. 10, the base of needle 1 may be provided with a multilayer coat, comprising e.g. layers 19, 20, 21 applied to the whole needle, and layer 22 applied only to sharpened portion 3 thereof. All these layers are cut away along plane 23, each layer being exposed to the surface of needle 1. This results in the formation of five different galvanic microcurrents (not shown), leading to a considerable intensification of the electrical action of needle 1 on epidermis 8, permitting the transfer of four various microelements, and thereby intensifying the effect of electrophoresis.

One or more layers of coat may be applied by spraying that results in formation of loose or dense layers. Loose layers of coat increase the flow of microelements, passing through them.

The order of location of materials on the needle, in the direction from the base toward the external layer, can be selected as follows:

Fe (steel)—Ni—Cu (or Pt, or Pd, or Au)—Ag;
Fe—Ni—Au;
Fe—Cr—Au;
Fe—Cr (or Ag, or Cu)—Cu (or Pt);
Fe—Zn—Cr;
Cu—Ag;
Cu—Ni—Cr.

The base of the needle is made of Fe or Cu or alloys thereof, e.g. steel or brass. Therefore, with the base made of Fe or steel, it is possible to apply coat layers of all the above metals in the specified order, e.g. first layer of nickel, second layer of copper (or platinum, or palladium, or gold), and third layer of silver. Copper or brass base may be coated with silver, gold, platinum, palladium, and nickel with a thin layer of chromium.

Needles of the above types may be also used for acupuncture. In the latter case, the heads member is replaced by a handle intended for fixing a physician's hand.

Still another object of the present invention comprises an applicator. As can be seen in FIGS. 11-12, the inventive applicator preferably comprises base member 5 with needles 24-32 fixed therein, at least a portion of needles 24-32 being provided with the area of contact between the needle and epidermis 8, said area formed by at least two materials having different electrochemical potentials. Needles 24-32 having different materials of base members and coats are located e.g. in the following order: one row 33 consists of solid copper needle 24; needle 25 having steel base and nickel coat and exposed sharpened portion 3; needle 26 having steel or iron base and solid copper coat layer 36 and silver (or gold, or platinum, or palladium) coat layer 37 on sharpened portion 3; needle 27 having iron or steel base with two-layer coat of zinc and chromium, and exposed sharpened portion 3; needle 28 having copper base and silver (or gold, or platinum, or palladium) coat on sharpened portion 3 etc. Another row 38 consists of needle 29 having copper or brass base and two-layer coat of nickel and chromium; copper needle 24; needle 30 with steel or iron base and two-layer coat of zinc and chromium; steel needle 31; needle 32 with copper or brass base and copper coat over the whole needle except sharpened portion 3 thereof etc. In subsequent rows, the order of location can be either similar or different; the critical point consists in that each needle has to be surrounded with needles whose bases and coats are made of different materials. Such arrangement accelerates electrophoresis and provides smoothing, as a result of reflexotherapy, the natural nonuniformity of the skin electrical field.

The applicator operates as follows:
Penetration of needles 24-32 into epidermis 8 generates the effect of mechanical irritation of a selected area of the user's body surface. At the same time, within the area of contact between needles 25, 26, 27, 28, 29, 30, 32 and the epidermis, $G_T$ galvanic microcurrents are generated (said microcurrents have been disclosed herein for various embodiments of the needles); these microcurrents have their action lines in the planes of needle axes and cause the effect of weak electrical fields on the area of the user's body. In addition, different electrical potentials of various needles cause generation of $G_r$ galvanic microcurrents between adjacent needles whose action lines are disposed in the planes perpendicular or inclined with respect to the action lines of microcurrents between materials of needles. These currents are imposed on galvanic microcurrents of individual needles, thereby generating a three-dimensional complicated heterogeneous electrical field in the user's epidermis. Various microelements are transferred from needles 24-32 into epidermis 8, the intensity of this transfer being amplified by microcurrents existing inside epidermis 8. Due to diversity of electrobiochemical conditions of epidermis 8 during interaction thereof with materials of needle surfaces, epidermis 8 performs automatic adjustment of microcurrent and electrophoresis parameters.

Arrangement of needles in the applicator, as well as base and coat materials are selected depending on the desired action of the applicator on selected areas of users' bodies (required intensity of mechanical action, electrical fields, saturation with certain microelements).

In the simplest case, the inventive applicator may use two kinds of needles, e.g. copper (brass) or steel needles, or needles having single type of coat/coats.

The needles may be also arranged in rows, each row being formed by the needles made of the same or similar materials, and differing by needle materials from the needles of other rows, thereby causing generation of a more uniform electrical field.

To manufacture needle bases and coats, the use can be made of chemical elements selected from the group comprising copper, iron, nickel, chromium, cobalt, aluminium, magnesium, zinc, tin, silver, titanium, vanadium, beryllium, gold, platinum, palladium, strontium, tellurium, and alloys and oxides thereof. This permits to produce durable and inexpensive needle bases provided with coats of small quantities of precious and rare materials, to expand the set of materials used, and thereby to create numerous galvanic couples generating numerous microcurrents having various parameters. This also permits the transfer of numerous microelements into the user's body.

I claim:

1. An applicator for use in reflexotherapy, comprising:
a flat elastic base member;
a plurality of needles fixed in said flat elastic base member;
each needle comprises a core, a sharpened portion with a pointed end, and a thickened portion;
said thickened portions are fixed in said flat elastic base member in such a way that the sharpened portions protrude from said flat elastic base member;
one or more groups of said needles have a partially coated core;
one or more groups of said needles have multilayer coatings of said core and sharpened portion but not at said pointed end of said sharpened portion thereof;
one or more groups of said needles differ from the other groups by the materials they are produced of or by the coating materials, which have different electrochemical potentials;
said needles and their coatings are fabricated from materials selected from a group comprising steel, copper, chromium, nickel, silver, cobalt, aluminum, magnesium, zinc, tin, titanium, vanadium, beryllium, gold, platinum, strontium, tellurium or their alloys and oxides;
said core is covered with coatings of different material layers;

said pointed end of said sharpened portion is free of coatings of different material layers; and each of said needles is placed on the base member in such a way that adjacent needles are made from materials and/or their alloys with different electrochemical potentials and are designed for contacting an user's skin.

2. An applicator according to claim 1, wherein:

at least a portion of said needles being made with solid and/or partial coats; and in the case of partial coat of said needle, the areas adjoining to their sharpened portions but not at said pointed ends thereof are made of at least two materials which have different electrochemical potentials.

3. An applicator for use in reflexotherapy, comprising:

a base member;

a plurality of needles fixed in said base member;

each said needle comprising a rod member having a sharp portion at a first end of said rod member, and a head portion at a second end thereof;

said sharp portion has a pointed end;

said head portion being wider than said rod member;

said rod member having a central longitudinal axis disposed in a first predetermined direction;

all head portions of said needles having major planar surfaces in a flat plane perpendicular to said first longitudinal axis of said rod member;

said needles being fixed in said base member so that said sharp portions protrude from said base member;

said rod member being made from a base material;

said needles including one or more first needles made from and/or coated with a first material, and one or more second needles made from and/or coated with a second material;

one or more third needles made from and/or coated with a third material having a different electrochemical potential than that of said first and second materials;

the coating on at least one of said needles comprises a multilayer coating of different materials;

the material in said needles and/or coatings being selected from steel, copper, chromium, nickel, silver, cobalt, aluminum, magnesium, zinc, tin, titanium, vanadium, beryllium, gold, platinum, palladium, strontium and tellurium or alloys or oxides thereof;

said first and second materials having different electrochemical potentials;

each said needle being adjacent to needles having base materials and coatings made from different materials;

said rod member is covered with coatings of different material layers;

said pointed end of said sharp portion is free of coatings of different material layers;

said needles being arranged in said base member in a configuration whereby, when adjacent needles having sharp portions are exposed to a surface of contact with a user's epidermis, said sharp portions but not said pointed ends thereof are either coated with and/or are made from different materials; and said partially-covered needles expose a surface of contact between each needle and the user's epidermis to at least said first and second materials.

* * * * *